US012636059B2

(12) United States Patent　　　(10) Patent No.:　US 12,636,059 B2

Rooks et al.　　　(45) Date of Patent:　**\*May 26, 2026**

(54) SYSTEMS AND METHODS OF COOLING SURGICAL INSTRUMENTS

(71) Applicant: Covidien LP, Mansfield, MA (US)

(72) Inventors: Kathy E. Rooks, Boulder, CO (US); Eric W. Larson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1394 days.

This patent is subject to a terminal disclaimer.

(21) Appl. No.: 16/710,026

(22) Filed: Dec. 11, 2019

(65) Prior Publication Data

US 2020/0107872 A1　　Apr. 9, 2020

Related U.S. Application Data

(63) Continuation of application No. 15/621,625, filed on Jun. 13, 2017, now Pat. No. 10,543,036.

(51) Int. Cl.

| | |
|---|---|
| *A61B 18/08* | (2006.01) |
| *A61B 17/32* | (2006.01) |
| *A61B 17/3209* | (2006.01) |
| *A61B 18/14* | (2006.01) |
| *A61B 18/18* | (2006.01) |
| *A61B 17/00* | (2006.01) |

(Continued)

(52) U.S. Cl.

CPC ............ *A61B 18/082* (2013.01); *A61B 17/32* (2013.01); *A61B 17/3209* (2013.01); *A61B 18/1402* (2013.01); *A61B 18/1815* (2013.01); *A61B 17/00* (2013.01); *A61B 2018/00011* (2013.01); *A61B 2018/00023* (2013.01); *A61B*

*2018/00029* (2013.01); *A61B 2018/00047* (2013.01); *A61B 2018/00577* (2013.01); *A61B 2018/00601* (2013.01); *A61B 2018/0063* (2013.01); *A61B 2217/007* (2013.01); *F04D 29/5866* (2013.01)

(58) Field of Classification Search

CPC .... A61B 2018/00023; A61B 2217/007; F04D 29/5866

See application file for complete search history.

(56) References Cited

U.S. PATENT DOCUMENTS

| | | | |
|---|---|---|---|
| 4,445,509 | A | 5/1984 | Auth |
| 5,304,214 | A | 4/1994 | DeFord et al. |

(Continued)

FOREIGN PATENT DOCUMENTS

| | | |
|---|---|---|
| CN | 1652328 A | 8/2005 |
| CN | 1658119 A | 8/2005 |

OTHER PUBLICATIONS

European Search Report dated Oct. 17, 2018, corresponding to European Application No. 18177179.1; 5 pages.

(Continued)

*Primary Examiner* — Jianying C Atkisson

*Assistant Examiner* — Khaled Ahmed Ali Al Samiri

(74) *Attorney, Agent, or Firm* — Carter, DeLuca & Farrell, LLP

(57) ABSTRACT

A fluid cooling system for cooling a microwave antenna includes an energy source configured to supply microwave energy to a microwave antenna for ablating tissue, a fluid source, a centrifugal pump, and a cooling member coupled to the centrifugal pump and configured to contact the tube to cool fluid flowing through the tube.

14 Claims, 9 Drawing Sheets

(51) Int. Cl.
    *A61B 18/00*         (2006.01)
    *F04D 29/58*         (2006.01)

(56)               References Cited

U.S. PATENT DOCUMENTS

| | | | |
|---|---|---|---|
| 5,899,077 A * | 5/1999 | Wright | H10N 10/00 |
| | | | 62/3.7 |
| 6,575,969 B1 | 6/2003 | Rittman et al. | |
| 7,027,304 B2 * | 4/2006 | Aisenbrey | F21V 29/76 |
| | | | 361/708 |
| 7,311,703 B2 | 12/2007 | Turovskiy et al. | |
| 7,918,092 B2 * | 4/2011 | Lin | F25B 21/02 |
| | | | 62/3.3 |
| 8,001,794 B2 * | 8/2011 | Windisch | F25B 21/02 |
| | | | 62/3.5 |
| 10,543,036 B2 | 1/2020 | Rooks et al. | |
| 2008/0058796 A1 | 3/2008 | O'Brien et al. | |
| 2008/0249521 A1 * | 10/2008 | Dunning | A61B 18/16 |
| | | | 606/35 |
| 2008/0269737 A1 | 10/2008 | Elmouelhi et al. | |
| 2009/0082837 A1 | 3/2009 | Gellman et al. | |
| 2009/0270954 A1 | 10/2009 | Schenck | |
| 2011/0071582 A1 | 3/2011 | Willyard et al. | |
| 2014/0276033 A1 | 9/2014 | Brannan et al. | |
| 2017/0049952 A1 | 2/2017 | Jezierski | |

OTHER PUBLICATIONS

Chinese Office Action dated May 24, 2021, issued in corresponding Chinese Appln. No. 201810604136, 17 pages.

Chinese Office Action dated Nov. 27, 2020, issued in corresponding Chinese Appln. No. 201810604136, with translated English summary, 9 pages.

Chinese Rejection Decision dated Jan. 11, 2022, issued in corresponding CN Appln. No. 201810604136, 12 pages.

Chinese Office Action dated Aug. 25, 2021, issued in corresponding CN Appln. No. 201810604136, 8 pages.

* cited by examiner

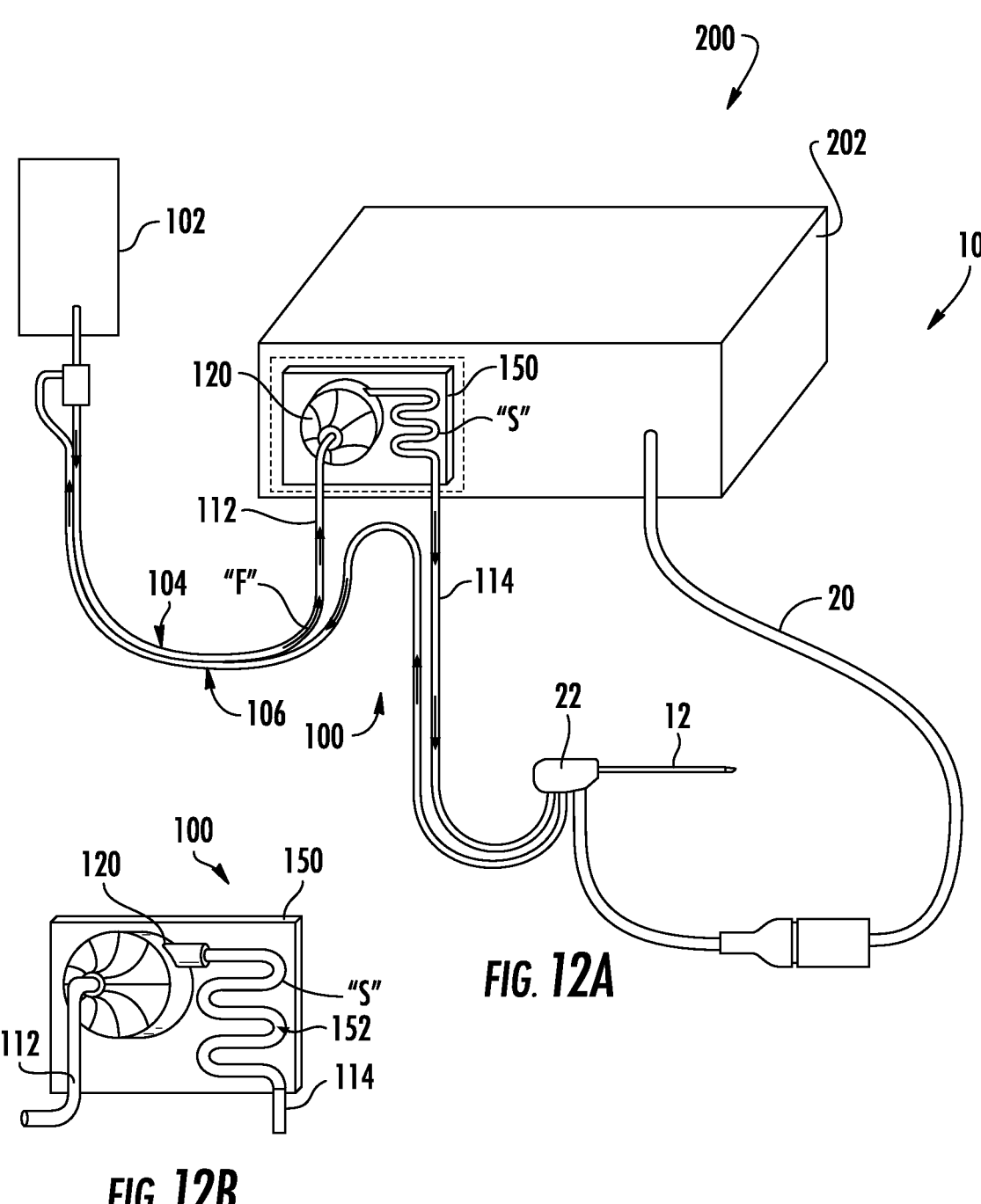
FIG. *12A*
FIG. *12B*

SYSTEMS AND METHODS OF COOLING SURGICAL INSTRUMENTS

CROSS-REFERENCE TO RELATED APPLICATION

This application is a continuation application of U.S. patent application Ser. No. 15/621,625, filed on Jun. 13, 2017, the entire contents of which are incorporated by reference herein.

BACKGROUND

1. Technical Field

The present disclosure relates to a cooling system, and more specifically, to a system and method for cooling an ablation instrument.

2. Discussion of Related Art

Presently, there are several types of electrosurgical probes used for the treatment of tumors. For example, microwave antennas may be inserted into a patient for the treatment of tumors by heating the tissue for a period of time sufficient to cause cell death and necrosis in the tissue region of interest. Such microwave antennas may be advanced into the patient, e.g., laparoscopically or percutaneously, and into or adjacent the tumor to be treated.

In transmitting the microwave energy into the tissue, the outer surface of a microwave antenna may heat up beyond a desired threshold temperature. To prevent overheating of a microwave antenna, several different cooling methodologies are conventionally employed. For example, some microwave antennas utilize balloons which are inflatable around selective portions of the antenna to cool the surrounding tissue. Other devices attempt to limit heating of tissue adjacent the antenna by selectively blocking the propagation of the microwave field generated by the antenna. These cooling systems also protect surrounding healthy tissues by selectively absorbing microwave radiation and minimize thermal damage to the tissue by absorbing heat energy. However, these conventional cooling methodologies may not be effective for cooling high power (e.g., 150 Watt) microwave ablation systems or for smaller gauge size microwave antennas. Accordingly, a need exists for a cooling system that effectively transfers heat away from high power and/or smaller gauge microwave antennas to maintain the microwave antenna below a threshold temperature.

SUMMARY

In one aspect of the present disclosure, a fluid cooling system for cooling a microwave antenna is provided. The fluid cooling system includes an energy source configured to supply microwave energy to a microwave antenna for ablating tissue, a fluid source, a centrifugal pump coupled to the energy source, and a cooling member coupled to the centrifugal pump. The fluid source is configured to deliver fluid to the microwave antenna for cooling the microwave antenna. The fluid source is coupled to the energy source via a first portion of a tube. The centrifugal pump is in fluid communication with the fluid source via the first portion of the tube and is configured to pump fluid to the microwave antenna via a second portion of the tube. The first and second portions of the tube are in fluid communication via the centrifugal pump. The cooling member is configured to contact the tube to cool fluid flowing through the tube.

In some embodiments, the cooling member may define a channel configured to receive the tube therein. The tube may be received flush in the channel. The channel may have an undulating configuration.

In some embodiments, a portion of the tube may be fabricated from a thermally conductive material.

In some embodiments, the fluid cooling system may further include a fan disposed within the energy source and configured to cause air to flow across the tube to cool the fluid.

In some embodiments, the cooling member may include a thermally conductive plate configured to passively cool the fluid.

In some embodiments, the cooling member may include a thermoelectric cooler configured to actively cool the fluid.

In another aspect of the present disclosure, a fluid cooling system for cooling a microwave antenna is provided. The fluid cooling system includes an energy source configured to supply microwave energy to a microwave antenna for ablating tissue, a fluid source configured to deliver fluid to the microwave antenna for cooling the microwave antenna, and a centrifugal pump coupled to the energy source and in fluid communication with the fluid source via a first portion of a tube. The fluid source is coupled to the microwave antenna via the tube. The centrifugal pump is configured to pump fluid to the microwave antenna via a second portion of the tube. The first and second portions of the tube are in fluid communication via the centrifugal pump.

In some embodiments, the fluid cooling system may further include a fan disposed within the energy source and configured to cause air to flow across the second portion of the tube to cool fluid flowing through the second portion of the tube.

In some embodiments, the second portion of the tube may be coupled to a vent in a housing of the energy source. The fan may be configured to draw air through the vent to cause the air to flow across the second portion of the tube.

In yet another aspect of the present disclosure, a fluid cooling system for use with a surgical instrument is provided. The fluid cooling system includes a tube, a pump, and a cooling member coupled to the pump. The tube includes a first portion and a second portion. The pump is configured to be in fluid communication with a fluid source via the first portion of the tube and configured to pump fluid from the fluid source to a surgical instrument via the second portion of the tube. The first and second portions of the tube are in fluid communication via the pump. The cooling member is disposed in contact with the tube to cool fluid flowing through the tube.

In some embodiments, the pump may be a centrifugal pump, and the cooling member may include a thermally conductive plate configured to passively cool the fluid.

In some embodiments, the cooling member may include a thermoelectric cooler configured to actively cool the fluid.

In some embodiments, the fluid cooling system may further include a plate configured to detachably couple to the cooling member. The tube may be disposed between and in contact with the cooling member and the plate.

In some embodiments, the cooling member and the plate may each define a channel. The tube may be configured to be received within each of the channels.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 12A is a perspective view of yet another embodiment of a surgical system including a fluid cooling system, a generator, and an ablation instrument; and FIG. 12B is a perspective view of a centrifugal pump, an inflow tube, and another embodiment of a cooling member of the fluid cooling system of FIG. 12A.

DETAILED DESCRIPTION

Figure 1:
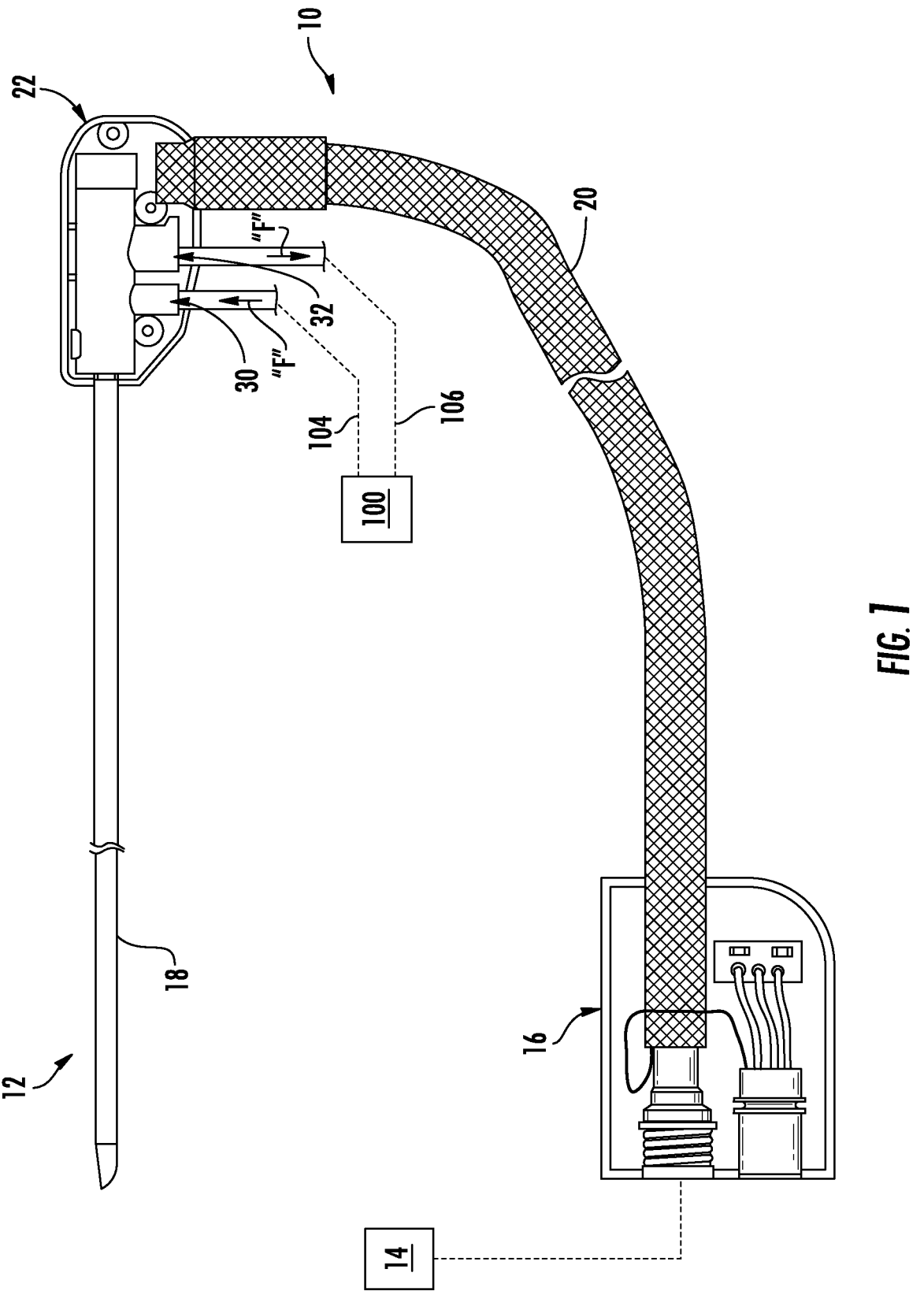
FIG. 1 is a schematic illustration of a microwave ablation system used for treating tissue.

Embodiments of the disclosed fluid cooling system for use with an ablation system and methods of use are described with reference to the accompanying drawings. Like reference numerals may refer to similar or identical elements throughout the description of the figures. As shown in the drawings and as used in this description, the term "proximal" refers to that portion of the described component that is closer to the user, and the term "distal" refers to that portion of the described component that is farther from the user.

As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as, for example, microwave ablation, radiofrequency (RF) ablation, or cryoablation. As it is used in this description, "fluid" generally refers to a liquid, a gas, or both. The term "coolant" may be used interchangeably with the term "fluid."

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the scope of the embodiments of the present disclosure as defined by the appended claims.

This disclosure relates generally to cooling systems that cool surgical instruments (e.g., an ablation probe) during use thereof. For example, in one embodiment, the present disclosure provides a fluid cooling system that includes a tube that transfers a fluid to and/or from an ablation probe, a centrifugal pump that conveys the fluid through the tube, and a cooling member that draws heat from the fluid within the centrifugal pump and/or the tube.

With reference to FIG. 1, a surgical system 10 is provided for treating tissue. Surgical system 10 generally includes a microwave ablation probe 12, a microwave generator 14, and a fluid cooling system 100. Generator 14 is configured to provide microwave energy at an operational frequency from about 500 MHz to about 5000 MHz, although other suitable frequencies are also contemplated. In some embodiments, generator 14 may generate any suitable type of energy, for example, RF energy, or ultrasonic energy.

Probe 12 and generator 14 are coupled to one another via a connector assembly 16 and a cable assembly 20. Connector assembly 16 is a cable connector suitable to operably connect cable assembly 20 to generator 14. Connector assembly 16 may house a memory (e.g., an EEPROM) storing a variety of information regarding various components of system 10. For example, the memory may store identification information that can be used by generator 14 to determine the identification of probes connected to generator 14. Based on the determined identification of a probe, generator 14 may or may not provide energy to the probe. For example, if the identification information stored in memory does not match identification information provided by the probe (e.g., via a RFID tag on the probe), generator 14 will not provide energy to the connected probe.

Cable assembly 20 interconnects connector assembly 16 and probe 12 to allow for the transfer of energy from generator 14 to probe 12. Cable assembly 20 may be any suitable, flexible transmission line, such as a coaxial cable, including an inner conductor, a dielectric material coaxially surrounding the inner conductor, and an outer conductor coaxially surrounding the dielectric material. Cable assembly 20 may be provided with an outer coating or sleeve disposed about the outer conductor. The sleeve may be formed of any suitable insulative material, and may be applied by any suitable method, e.g., heat shrinking, overmolding, coating, spraying, dipping, powder coating, and/or film deposition.

Probe 12 includes a radiating portion 18 that radiates energy provided by generator 14. Radiating portion 18 is coupled to cable assembly 20 through a handle assembly 22. Handle assembly 22 has an inlet fluid port 30 and an outlet fluid port 32 each in fluid communication with an interior chamber (not explicitly shown) defined in probe 12. Ports 30 and 32 of the handle assembly 22 are coupled to a supply tank 102 (FIG. 2) of the fluid cooling system 100 via inflow and outflow tubes 104, 106 of the fluid cooling system 100, respectively. Thus, coolant fluid "F," supplied and circulated by the fluid cooling system 100, may circulate from inlet fluid port 30 around the interior chamber or chambers of probe 12 to cool probe 12 during use, and then out of outlet fluid port 32.

For a more detailed description of various components of an exemplary microwave ablation system, reference may be made to U.S. Patent Application Publication No. 2014/0276033, filed on Mar. 15, 2013, the entire contents of which are incorporated by reference herein.

Figure 2:
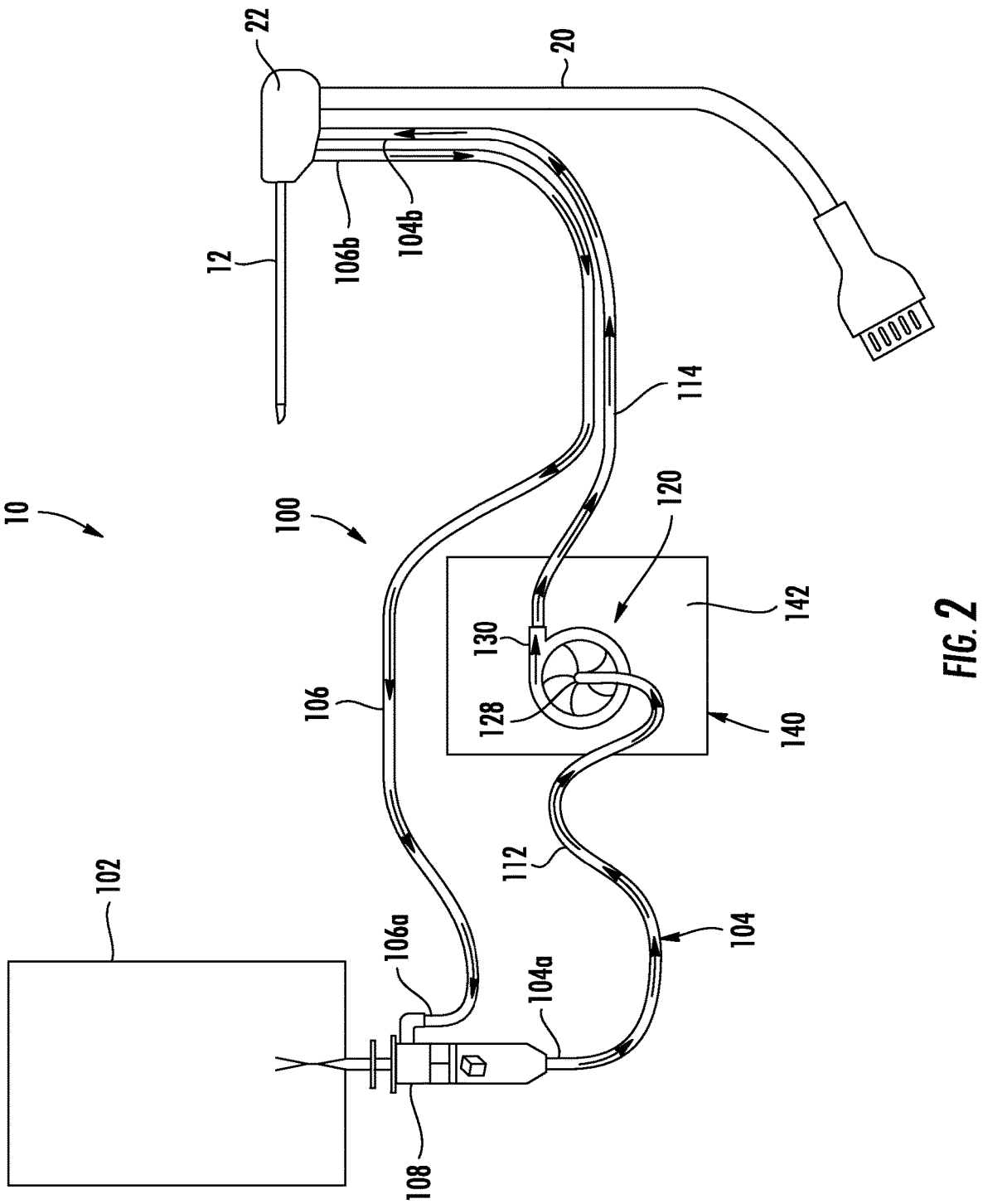
FIG. 2 is a plan view of an embodiment of a fluid cooling system coupled to an ablation instrument of the microwave ablation system of FIG. 1.

With reference to FIG. 2, details of an embodiment of the fluid cooling system 100 of the surgical system 10 will be described. The fluid cooling system 100 is configured to cool and circulate fluid through probe 12 to maintain probe 12 at a temperature at or below a threshold temperature. Fluid cooling system 100 generally includes the supply tank 102, inflow and outflow tubes 104, 106, a supply pump 120, and a cooling member 140 for passively and/or actively cooling the fluid "F." The supply tank 102 stores the fluid and, in one embodiment, may maintain the fluid at a predetermined temperature. In embodiments, the supply tank 102 may be an IV bag containing a saline solution or any other suitable fluid.

Each of the inflow and outflow tubes 104, 106 of the fluid cooling system 100 has a first end 104a, 106a and a second end 104b, 106b, respectively. The first end 104a, 106a of each of the inflow and outflow tubes 104, 106, respectively, is fluidly coupled to the supply tank 102. In some embodiments, the first end 104a, 106a of each of the inflow and outflow tubes 104, 106, respectively, may be fluidly coupled to the supply tank 102 via a drip chamber 108. The second end 104b of the inflow tube 104 is fluidly coupled to inlet fluid port 30 of the handle assembly 22 to facilitate delivery of fluid from the supply tank 102 into probe 12. The second end 106b of the outflow tube 106 is fluidly coupled to the outlet fluid port 32 of the handle assembly 22 to facilitate delivery of fluid out of the probe 22 to the supply tank 102.

The inflow tube 104 of the fluid cooling system 100 includes two portions 112, 114 that are fluidly interconnected by the supply pump 120. The first portion 112 of the inflow tube 104 interconnects the supply tank 102 and an inlet 128 of the supply pump 120, and the second portion 114 of the inflow tube 104 interconnects an outlet of the supply pump 120 and the probe 12.

Figure 3:
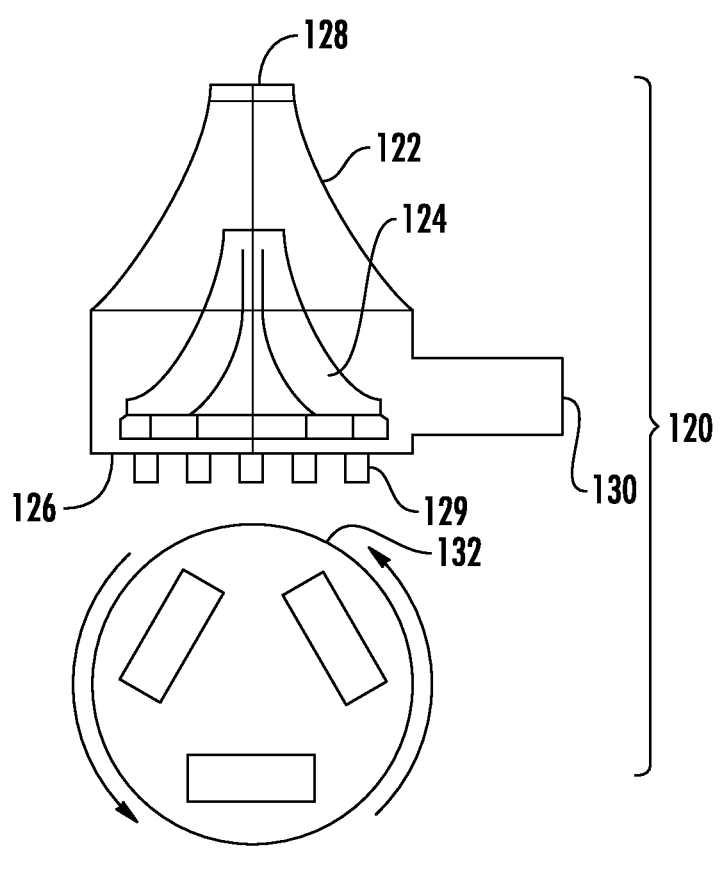
FIG. 3 is a plan view, with parts separated, of an embodiment of a centrifugal pump of the fluid cooling system of FIG. 2.

With reference to FIGS. 2 and 3, the supply pump 120 of the fluid cooling system 100 is responsible for the continuous delivery of the fluid from the supply tank 102 to the probe 12 via the inflow tube 104, and back to the supply tank 102 via the outflow tube 106. In particular, the supply pump 120 is a centrifugal pump that includes a casing 122 and a motor-driven impeller 124 disposed within the casing 122. The casing 122 has a base 126 fabricated from a material with a high thermal conductivity, such as, for example, stainless steel. The base 126 may be planar, as shown in the illustrated embodiment of FIG. 3, or any other suitable configuration. The casing 122 defines the inlet 128 and the outlet 130 of the supply pump 120. In some embodiments, the inlet 128 and the outlet 130 may be oriented at a perpendicular angle relative to one another. The impeller 124 is in direct contact with a motor 132, which drives a rotation of the impeller 124. In embodiments, the motor 132 may be a rotary motor or a magnetic motor.

A rotation of the impeller 124 due to actuation by the motor 132 creates suction at the inlet 128, thereby inducing the fluid to flow from the first portion 112 of the inflow tube 104 into the inlet 128 of the centrifugal pump 120, which pushes the fluid out of the centrifugal pump 120 via the outlet 130 of the centrifugal pump 120 and into the second portion 114 of the inflow tube 104. Implementing a centrifugal pump in the fluid cooling system 100 of the present disclosure may generate a relatively higher and more constant flow rate than conventional pumps, which leads to more efficient cooling of the cooling fluid. In embodiments, the centrifugal pump 120 may be coupled to the outflow tube 106 rather than the inflow tube 104.

It is contemplated that the centrifugal pump 120 described herein may operate in a similar manner as the Affinity CP Centrifugal Blood Pump by Medtronic®. In other embodiments, the supply pump may be a peristaltic pump or any other suitable pump configured to circulate fluid from the supply tank 102 and into the probe 12.

Figure 4:
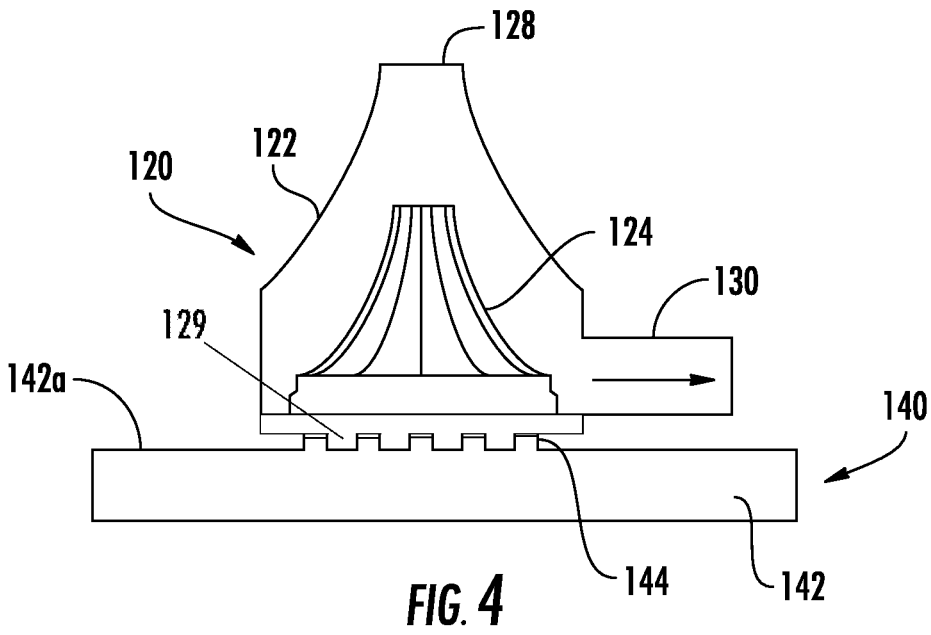
FIG. 4 is a side view of the centrifugal pump of FIG. 3 coupled with an embodiment of a cooling member of the fluid cooling system of FIG. 2.

With reference to FIGS. 2 and 4, the cooling member 140 of the fluid cooling system 100 includes a heat sink plate 142 for passively cooling the cooling fluid "F." The heat sink plate 142 may have a planar or other suitable configuration and is fabricated from a material with a high thermal conductivity, such as, for example, copper, aluminum alloy, stainless steel, a metallic composite, or any material having a thermal conductivity sufficient to rapidly draw away heat present in the fluid "F" flowing through the segment "s" of the inflow tube 104. The base 126 of the casing 122 of the centrifugal pump 120 is directly attached to an upper surface 142a of the heat sink plate 142 such that heat generated by the centrifugal pump 120 and/or heat present in the fluid "F" flowing through the centrifugal pump 120 is transferred directly from the base 126 of the casing 122 of the centrifugal pump 120 to the heat sink plate 142 of the cooling member 140. In this way, the heat sink plate 142 passively cools the fluid "F" flowing through the fluid cooling system 100.

The upper surface 142a of the heat sink plate 142 may have a plurality of heat sink steps 144 configured to interface with corresponding heat conductive surface features 129 (FIG. 3) extending from the base 126 of the casing 122 of the centrifugal pump 120. When the surface features 129 of the centrifugal pump 120 interface or interdigitate with the heat sink steps 144 of the heat sink plate 142, heat transfer from the centrifugal pump 120 to the heat sink plate 142 is enhanced.

Figure 5:
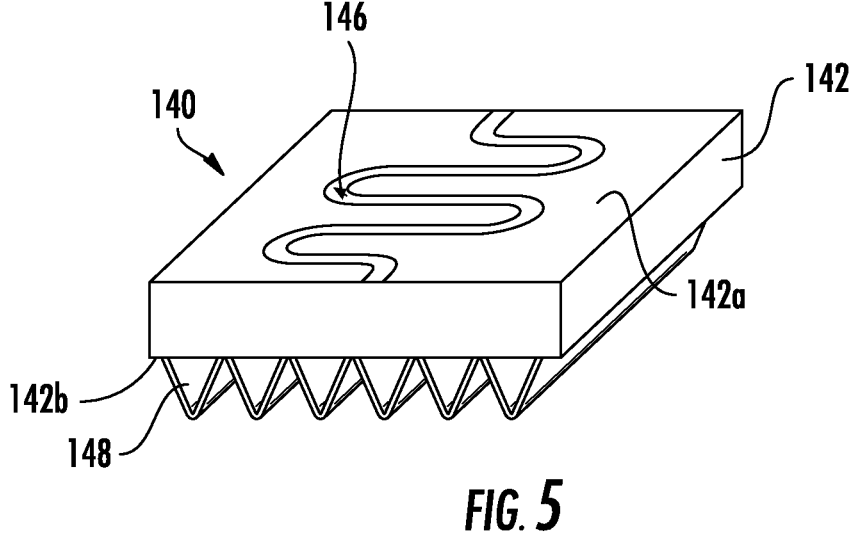
FIG. 5 is a perspective view of another embodiment of a cooling member of the fluid cooling system of FIG. 2.
Figure 6:
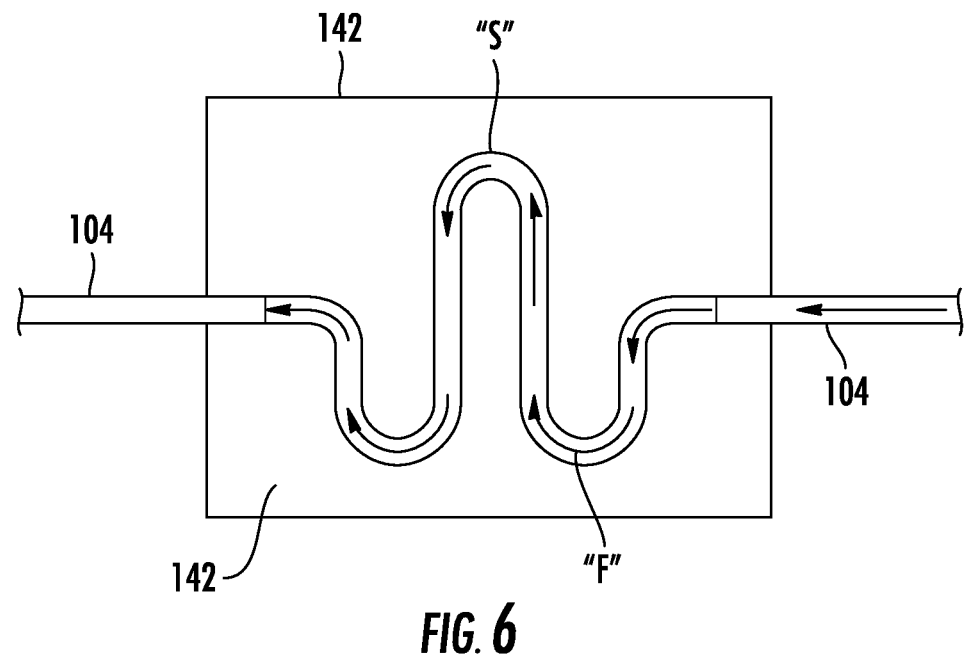
FIG. 6 is a top view illustrating an inflow tube of the fluid cooling system attached to the cooling member of FIG. 5.

With reference to FIGS. 5 and 6, in one embodiment, the heat sink plate 142 of the cooling member 140 may define a channel 146 in the upper surface 142a thereof. The cooling member 140 may include a plurality of heat sinks feature 148 (e.g., fins, folds, pins) extending from a bottom surface 142b of the heat sink plate 142. The purpose of the heat sink feature 148 is to increase surface area for efficient heat transfer. The channel 146 may extend along the entire length of the heat sink plate 142 or along a portion of the heat sink plate 142, and may assume an undulating or tortuous path. The channel 146 is configured to receive a segment "s" of the inflow tube 104. The segment "s" of the inflow tube 104 may be received flush in the channel 146 (e.g., an outer surface of the segment "s" is nested within the channel 146) to facilitate the transfer of heat from the fluid "F" flowing through the segment "s" of the inflow tube 104 to the heat sink plate 142.

In embodiments, the segment "s" of the inflow tube 104 may be fabricated from a material that has a greater thermal conductivity than the remaining portions of the inflow tube 104. For example, the segment "s" of the inflow tube 104 disposed within the channel 146 of the heat sink plate 142 may be fabricated from metal tubing, and the remaining portions of the inflow tube 104 may be fabricated from PVC tubing. In other embodiments, a segment of the outflow tube 106, rather than the inflow tube 104, may be received in the channel 146 of the heat sink plate 142 for cooling the fluid flowing through the outflow tube 104.

Figures 7, 8:
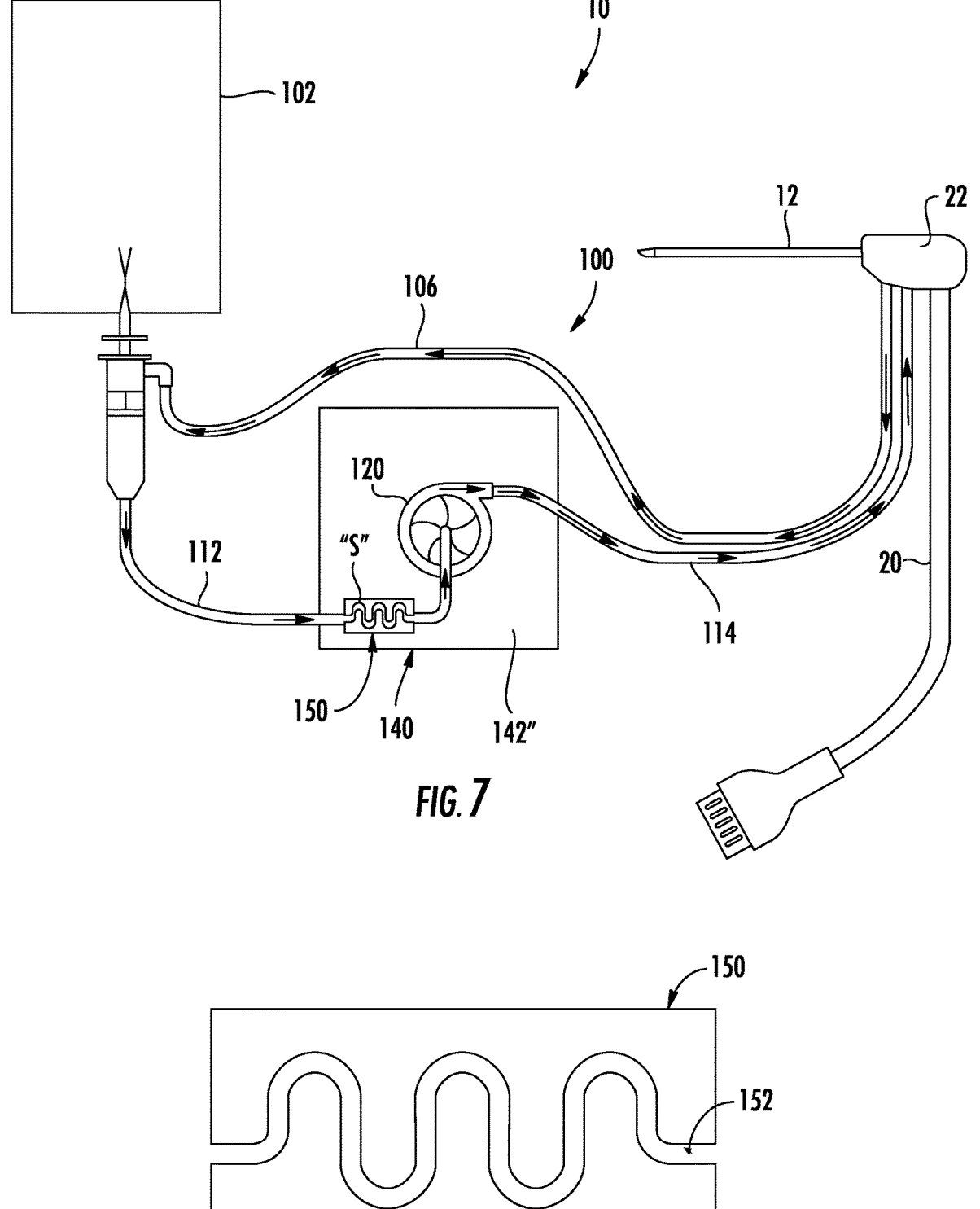
FIG. 7 is a plan view of another embodiment of a fluid cooling system coupled to an ablation instrument of the microwave ablation system of FIG. 1.
FIG. 8 is a top view of an embodiment of an active cooling member of the fluid cooling system of FIG. 7.

With reference to FIGS. 7 and 8, in one embodiment, the cooling member 140 may also include a thermoelectric cooler 150 for actively cooling the fluid "F" passing through the fluid cooling system 100. The thermoelectric cooler 150 may be attached to the upper surface 142a of the heat sink plate 142. In embodiments, rather than the thermoelectric cooler 150 being used as an add-on to the heat sink plate 142, the thermoelectric cooler 150 may be a substitute for the heat sink plate 142, and therefore may serve as a stand-alone component of the fluid cooling system 100 for actively cooling the fluid "F." The thermoelectric cooler 150 actively reduces the temperature of the fluid "F" using, for example, thermoelectric Peltier principles.

More specifically, the segment "s" of the inflow tube 104 is in direct contact with the thermoelectric cooler 150 to facilitate the transfer of heat from the fluid "F" flowing through the segment "s" to the thermoelectric cooler 150. The segment "s" of the inflow tube 104 may have an undulating or tortuous configuration to increase the amount of contact the segment "s" of the inflow tube 104 has with the thermoelectric cooler 150. The thermoelectric cooler 150 may define a channel 152 extending along a length thereof. The channel 152 may assume an undulating or tortuous configuration corresponding to the configuration of the segment "s" of the inflow tube 104. The channel 152 is configured for receipt of the segment "s" of the inflow tube 104 such that a substantial portion of a peripheral surface of the segment "s" of the inflow tube 104 is in contact with the thermoelectric cooler 150. In some embodiments, the segment "s" of the inflow tube 104 may be enclosed within the thermoelectric cooler 150 such that the entire peripheral surface of the segment "s" is in contact with the thermoelectric cooler 150. One skilled in the art will recognize that there are a number of cooling technologies besides thermoelectric coolers that may be used for actively cooling the fluid, including, for example, recirculating chilled fluid, vapor compression elements, or phase change cryogenic devices.

Figures 9A, 9B, 9C:
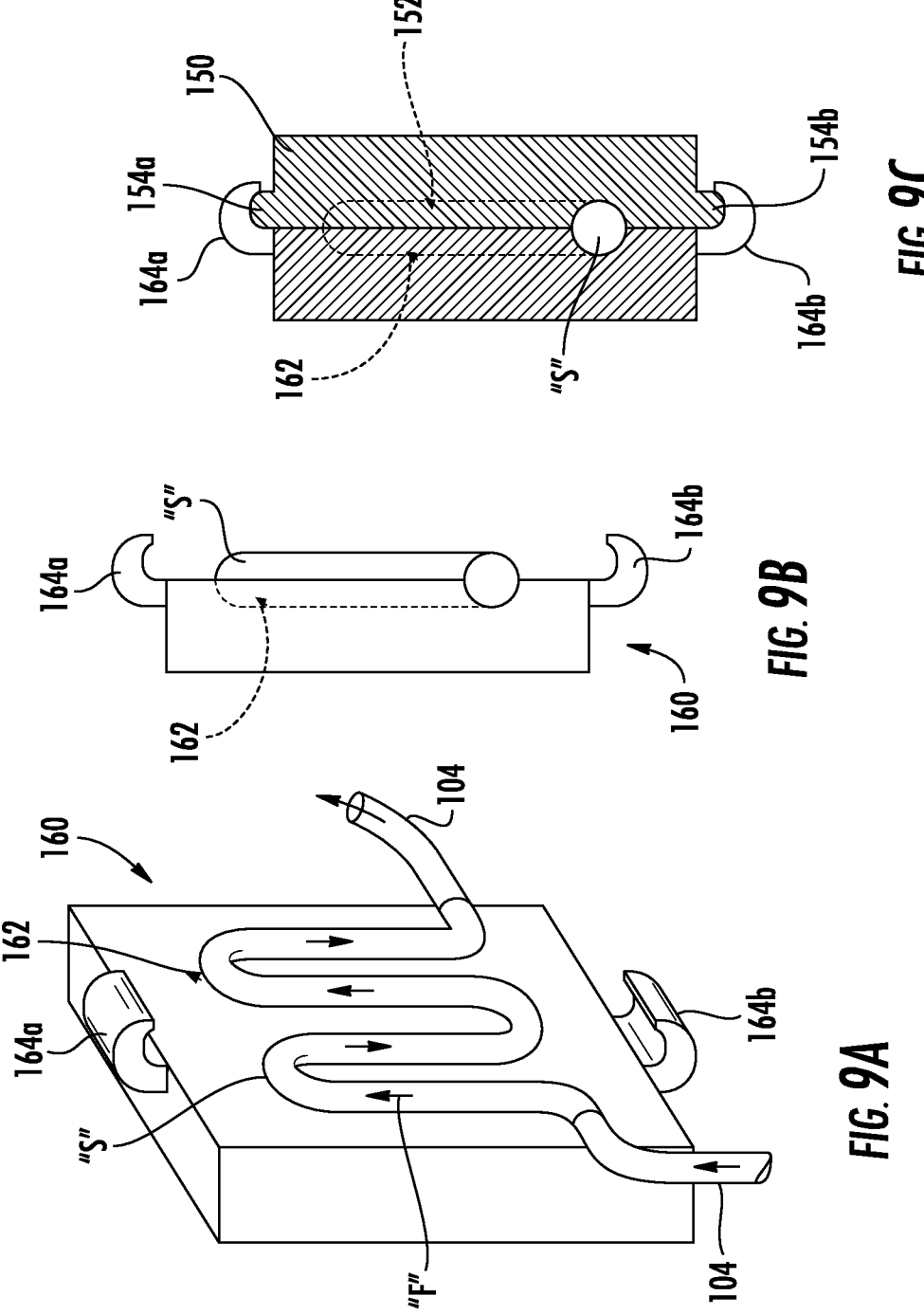
FIG. 9A is a side, perspective view illustrating the inflow tube of the fluid cooling system of FIG. 7 attached to a plate.
FIG. 9B is a side view illustrating the inflow tube attached to the plate of FIG. 9A.
FIG. 9C is a cross-sectional side view illustrating the inflow tube coupled between the plate of FIG. 9A and the active cooling member of FIG. 8.

With reference to FIGS. 9A-9C, in some embodiments, the fluid cooling system 100 may include a tubing plate 160 that is configured to detachably couple to the thermoelectric cooler 150. In embodiments, the tubing plate 160 may be configured to detachably couple to the heat sink plate 142 (FIGS. 5 and 6) of the cooling member 140 instead of the thermoelectric cooler 150. The tubing plate 160 may be fabricated from a non-metallic material and defines a channel 162 along a length thereof. The channel 162 is configured to receive the segment "s" of the inflow tube 104 therein. The tubing plate 160 has a pair of hooks 164a, 164b extending from opposite sides of the tubing plate 160. The hooks 164a, 164b are configured to engage tabs 154a, 154b extending from opposite sides of the thermoelectric cooler 150 to detachably couple the tubing plate 160 to the thermoelectric cooler 150. When the tubing plate 160 is coupled to the thermoelectric cooler 150 via the mating engagement of the respective hooks 164a, 164b and tabs 154a, 154b, the channel 162 of the tubing plate 160 and the channel 152 of the thermoelectric cooler 150 are aligned with one another to cooperatively form a continuous, undulating passageway that at least partially encloses the segment "s" of the inflow tube 104 when the segment "s" is disposed between the tubing plate 160 and the thermoelectric cooler 150 for optimal surface contact with the tubing plate 160 and the thermoelectric cooler 150.

Figures 10A, 10B, 10C:
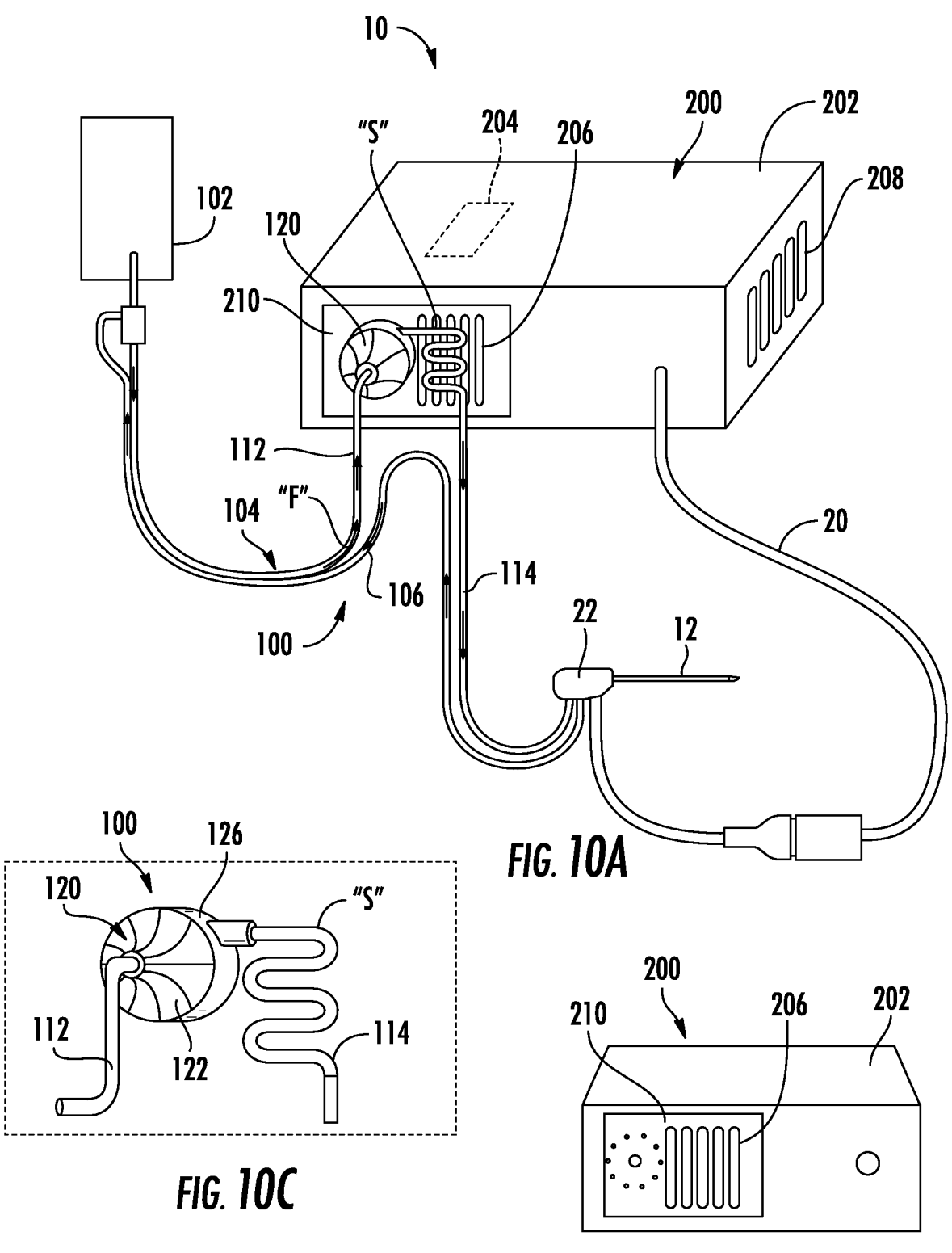
FIG. 10A is a perspective view of yet another embodiment of a surgical system including a fluid cooling system, a generator, and an ablation instrument.
FIG. 10B is a perspective view of the generator of the surgical system of FIG. 10A without the fluid cooling system coupled thereto.
FIG. 10C is a plan view of a centrifugal pump fluidly coupled to an inflow tube of the fluid cooling system of FIG. 10A.

With reference to FIGS. 10A-10C, another embodiment of a generator 214 for use with the fluid cooling system 100 is shown. The generator 200 includes a housing 202 and a fan 204 disposed within the housing 202. The housing 202 includes an inflow vent 206 and an outflow vent 208 such that air is drawn into the housing 202 via suction created by the fan 204 and is expelled from the housing 202 via the outflow vent 208. The inflow vents 206 may be defined through a metallic substrate 210 attached to the housing 202 of the generator 200.

The base 126 of the casing 122 of the centrifugal pump 120 and the segment "s" of the inflow tube 104 are each secured, either detachably or fixedly, to the metallic substrate 210 of the generator 200. The metallic substrate 210 functions as a heat sink and absorbs heat directly from the centrifugal pump 120 and the segment "s" of the inflow tube 104. In embodiments, the generator 200 may be devoid of the metallic substrate 210 such that the centrifugal pump 120 and the segment "s" of the inflow tube 104 are both directly attached to the housing 202 of the generator 200.

In operation, when the fan 204 is activated, the fan 204 draws air through the inflow vents 206 such that the drawn air moves across the centrifugal pump 120 and the segment "s" of the inflow tube 104. As the drawn air moves across the centrifugal pump 120 and the segment "s" of the inflow tube 104, the air flows around the centrifugal pump 120, the segment "s" of the inflow tub 104, and the metallic substrate 210 cooling the fluid "F" through thermal convection prior to entering the probe 12. This can also be done with the outflow tube 106 by cooling the heated fluid "F" when it exits the probe 12 and is re-circulated into the supply tank 102.

Figures 11A, 11B:
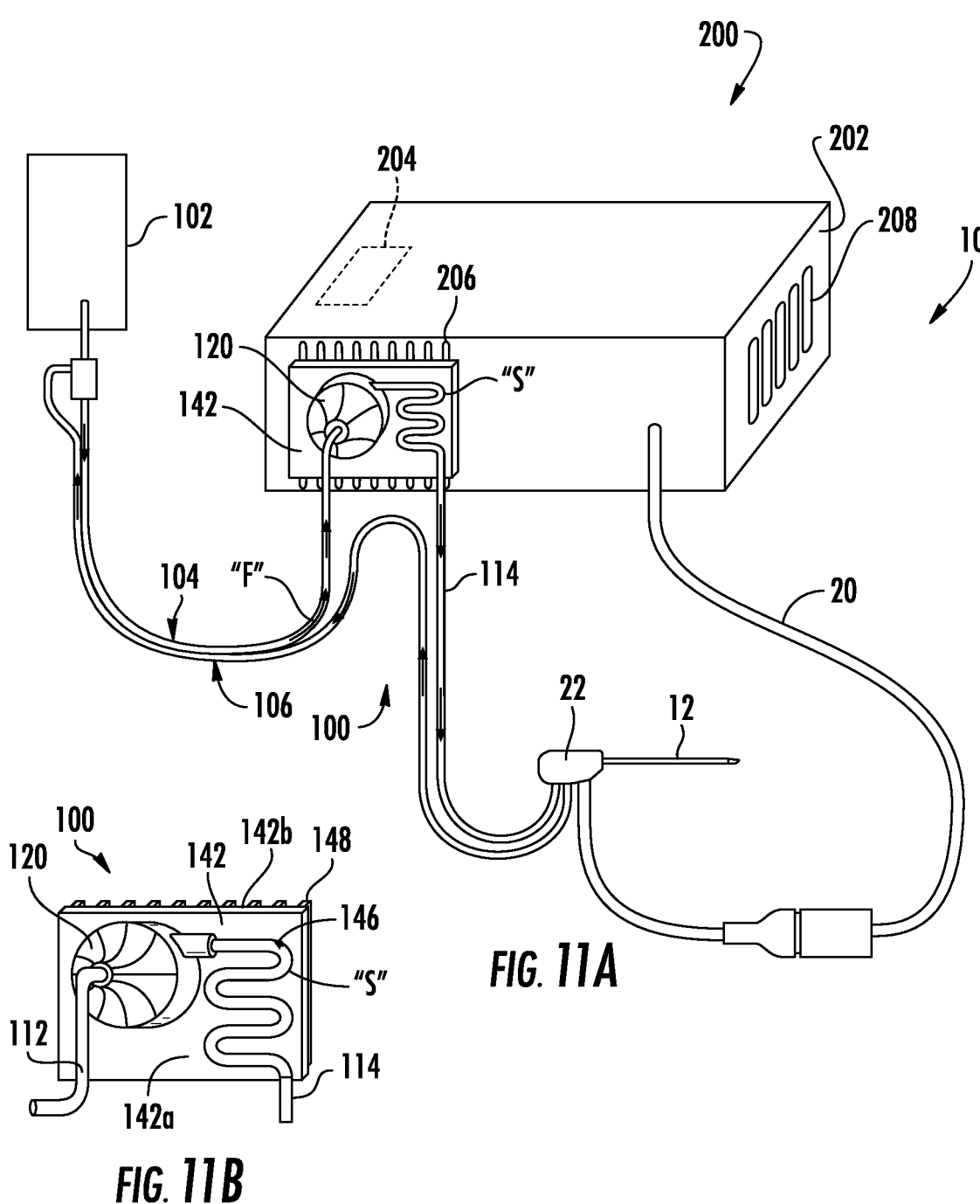
FIG. 11A is a perspective view of yet another embodiment of a surgical system including a fluid cooling system, a generator, and an ablation instrument.
FIG. 11B is a perspective view of a centrifugal pump, inflow tube, and an embodiment of a cooling member of the fluid cooling system of FIG. 11A.

With reference to FIGS. 11A and 11B, another embodiment of the fluid cooling system 100 of the present disclosure is shown. In this embodiment, the heat sink plate 142 of the fluid cooling system 100 is directly attached to the housing 202 of the generator 200 adjacent the inflow vents 206. The heat sink feature 148 extending from the bottom surface 142b of the heat sink plate 142 may be attached to the housing 202 of the generator 200. In embodiments, the heat sink feature 148 is a plurality of metallic fins configured to extend through the inflow vents 206 such that at least a portion of the metallic fins are disposed within the housing 202 and are oriented toward the fan 204. The centrifugal pump 120 and the segment "s" of the inflow tube 104 are attached to the upper surface 142a of the heat sink plate 142. The segment "s" of the inflow tube 104 is received within the channel 146 defined in the upper surface 142a of the heat sink plate 142 to facilitate heat transfer from the segment "s" to the heat sink plate 142.

In operation, when the fan 204 is activated, the fan 204 draws air through the inflow vents 206 such that the drawn air moves across the heat sink feature 148 to cool the heat sink plate 142. As the heat sink plate 142 is cooled, the heat sink plate 142 draws heat away from the fluid "F" flowing through the centrifugal pump 120 and the segment "s" of the inflow tube 104, thereby cooling the fluid "F" prior to entering the probe 12.

With reference to FIGS. 12A and 12B, another embodiment of the fluid cooling system 100 of the present disclosure is shown. In this embodiment, instead of the heat sink plate 142 (FIGS. 5 and 6) of the fluid cooling system 100 being attached to the housing 202 of the generator 200, the thermoelectric cooler 150 of the fluid cooling system 100 is attached to the housing 202 of the generator 202. In embodiments, the thermoelectric cooler 150 may be detachably or fixedly attached to the housing 202 of the generator 200. The centrifugal pump 120 and the segment "s" of the inflow tube 104 are supported on the upper surface of the thermoelectric cooler 150. In embodiments, the segment "s" of the inflow tube 104 may be received within the channel 152 defined in the upper surface of the thermoelectric cooler 150 to facilitate heat transfer from the segment "s" to the thermoelectric cooler 150.

During operation, the thermoelectric cooler 150 actively cools itself, thereby drawing heat away from the fluid "F" flowing through the centrifugal pump 120 and the segment "s" of the inflow tube 104. As such, the fluid "F" is actively cooled prior to entering the probe 12.

It should be appreciated that any of the various embodiments of the fluid cooling system described herein may be configured to be attached, either detachably or fixedly, to the generator of the surgical system or a cart (not shown) of the surgical system.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A fluid cooling system for use with a surgical instrument, comprising:
    a tube;
    a centrifugal pump having a housing including a base, the centrifugal pump configured to be in fluid communication with a fluid source and the tube to pump fluid from the fluid source to a surgical instrument via the tube;
    a thermoelectric cooler configured to actively cool itself and defining a first channel configured to receive the tube, the thermoelectric cooler being directly coupled to the housing of the centrifugal pump and to the tube to actively cool the centrifugal pump and fluid flowing through the tube, wherein the thermoelectric cooler includes a plurality of steps interlocked with a plurality of surface features extending from the base of the housing; and
    a tubing plate configured to passively cool fluid flowing through the tube and to detachably couple directly to the thermoelectric cooler, the tubing plate defining a second channel configured to receive the tube, wherein upon detachable direct coupling of the thermoelectric cooler with the tubing plate the first and second channels align to cooperatively form a continuous passageway that encloses the tube such that the tube is maintained in contact with the thermoelectric cooler and the tubing plate.

2. The fluid cooling system according to claim 1, wherein each of the first and second channels has an undulating configuration.

3. The fluid cooling system according to claim 1, wherein at least a portion of the tube is fabricated from a thermally conductive material.

4. The fluid cooling system according to claim 1, wherein the continuous passageway extends through opposing ends of each of the cooler and the tubing plate.

5. A fluid cooling system for use with a microwave ablation probe, comprising:
    a thermoelectric cooler configured to actively cool itself and defining a first channel configured for receipt of a tube;
    a centrifugal pump having a housing directly coupled to the thermoelectric cooler, wherein the thermoelectric cooler includes a plurality of steps interlocked with a plurality of surface features extending from a base of the housing; and
    a tubing plate defining a second channel configured for receipt of the tube, the tubing plate configured to detachably couple directly to the thermoelectric cooler, wherein when the tubing plate and the thermoelectric cooler are directly coupled to one another, the first and second channels are aligned with one another to cooperatively form a continuous passageway to enclose the tube therein.

6. The fluid cooling system according to claim 5, further comprising the tube, wherein the tube is configured to transfer cooling fluid to the microwave ablation probe.

7. The fluid cooling system according to claim 5, wherein the tubing plate or the thermoelectric cooler has a pair of hooks extending from opposite sides thereof, and the other of the tubing plate or the thermoelectric cooler has a pair of tabs extending from opposite sides thereof, the pair of hooks configured to engage the pair of tabs to detachably couple the tubing plate to the thermoelectric cooler.

8. The fluid cooling system according to claim 5, wherein the tubing plate is fabricated from a non-metallic material.

9. The fluid cooling system according to claim 5, wherein the continuous passageway extends through opposing ends of each of the thermoelectric cooler and the tubing plate.

10. A fluid cooling system for use with a microwave ablation probe, comprising:
    an inflow tube;
    a centrifugal pump having a housing including a base, the centrifugal pump configured to be in fluid communication with a fluid source and the inflow tube to pump fluid from the fluid source to a microwave ablation probe via the inflow tube;
    a thermoelectric cooler configured to actively cool itself, the thermoelectric cooler being directly coupled to the housing of the centrifugal pump and to the inflow tube to actively cool the centrifugal pump and the fluid flowing through the inflow tube, wherein the thermoelectric cooler includes a plurality of steps interlocked with a plurality of surface features extending from the base of the housing; and
    a tubing plate configured to detachably couple directly to the thermoelectric cooler, such that the inflow tube is disposed between the thermoelectric cooler and the tubing plate when the thermoelectric cooler and the tubing plate are directly coupled to one another.

11. The fluid cooling system according to claim 10, wherein each of the tubing plate and the thermoelectric cooler defines a channel configured for receipt of the inflow tube.

12. The fluid cooling system according to claim 11, wherein when the tubing plate and the thermoelectric cooler are coupled to one another, the channels of the thermoelectric cooler and the tubing plate are aligned with one another to cooperatively form a continuous passageway to enclose the inflow tube therein.

13. The fluid cooling system according to claim 12, wherein the continuous passageway extends through opposing ends of each of the thermoelectric cooler and the tubing plate.

14. The fluid cooling system according to claim 10, wherein the tubing plate or the thermoelectric cooler has a pair of hooks extending from opposite sides thereof, and the other of the tubing plate or the thermoelectric cooler has a pair of tabs extending from opposite sides thereof, the pair of hooks configured to engage the pair of tabs to detachably couple the tubing plate to the thermoelectric cooler.

\*   \*   \*   \*   \*